United States Patent [19]

Slimak

[11] Patent Number: 5,204,137

[45] Date of Patent: * Apr. 20, 1993

[54] PROCESSES FOR PRODUCTS FROM SWEET POTATO

[76] Inventor: Karen M. Slimak, P.O. Box 2444, Springfield, Va. 22152

[*] Notice: The portion of the term of this patent subsequent to May 15, 2007 has been disclaimed.

[21] Appl. No.: 522,820

[22] Filed: May 14, 1990

Related U.S. Application Data

[63] Continuation-in-part of Ser. No. 825,656, Jan. 31, 1986, Pat. No. 4,925,697, and a continuation-in-part of Ser. No. 294,690, Aug. 1, 1988.

[51] Int. Cl.⁵ ............................................. A23L 1/214
[52] U.S. Cl. .................................... 426/637; 426/518; 426/524; 426/549; 426/552; 426/562; 426/801; 426/804
[58] Field of Search ............... 426/549, 637, 640, 518, 426/523, 524, 552, 801, 804, 562, 601

[56] References Cited

FOREIGN PATENT DOCUMENTS 104850  8/1980  Japan ..................................... 426/637

OTHER PUBLICATIONS

Ciacco, "Tubers:Composition & use in bread baking", Dissertation Abstracts Int B (1977) 38(4) p. 1480.
Casier et al., "Bread Production from pure flours of tropical starchy crops", Tropical Foods Chem & Nutut. Academic Press N.Y., vol. 1 (1979) pp. 279-340.
Snack Food Journal Feb. 1980, p. 20.
Radford et al., 1964, Guide to the vascular flora of the Carolinas, The Book Exchange, University of North Carolina, Chapel Hill, N.C., pp. 3-29, 273-276.
Peterson, Lee A., 1977, A field guide to wild edible plants of Eastern and Central North America, Houghton Mifflin Company, Boston, MA. p. 20.

*Primary Examiner*—R. B. Penland
*Attorney, Agent, or Firm*—Stevens, Davis, Miller & Mosher

[57] ABSTRACT

A variety of different food products, prepared from edible tubers of the morning glory family, Convolvulaceae. are substitutes for wheat and other grains, milk, eggs, and a partial substitute for nuts.

15 Claims, No Drawings

PROCESSES FOR PRODUCTS FROM SWEET POTATO

RELATED APPLICATIONS

The present application is a Continuation in Part of U.S. Pat. application Ser. No. 825,656, filed on Jan. 31, 1986, U.S. Pat. No. 4,925,697, titled, "Processes of Products from Sweet Potato", the entire disclosure of which is herein incorporated by reference. and also U.S. Pat. application Ser. No. 294,690, filed on Aug. 1. 1988, titled, "Flour, Bread, Milk and Other Products from White Sweet Potatoes, Cassava, Edible Aroids, Amaranth, Yams and Lotus", the entire disclosure of which is herein incorporated by reference.

In my previous application Ser. No. 825,656, I disclosed the following: A variety of different food products, prepared from tubers with light-colored flesh varieties of the morning glory family Convolvulaceae, are substitutes for wheat and other grains, milk, eggs, and a partial substitute for nuts.

In my previous U.S. Pat. application Ser. No. 294,690, I disclosed flours of light-colored flesh varieties of the morning glory family. Convolvulaceae, with broader ranges of non-farinaceous material present and with broader ranges of particle sizes also having suitable baking properties and serving as substitutes for wheat and other grains, milk, eggs, and a partial substitute for nuts.

I have now found that the properties I previously described only as possible from white sweet potatoes and other tubers with light colored flesh of the morning glory family. Convolvulaceae, may be obtained from all tubers of family Convolvulaceae, including tubers at least more deeply colored than light-fleshed tubers. including yellow and orange varieties and including regardless of color, varieties with firm flesh and varieties with moist flesh.

BACKGROUND OF THE INVENTION (1) Field of Invention

The present invention is concerned with the utilization of all tubers of family Convolvulaceae, including tubers at least more deeply colored than light-fleshed tubers, including yellow and orange varieties, and including regardless of color, varieties with firm flesh and varieties with moist flesh, with the purpose of producing various flours from the tubers, and other valuable edible products and industrial products.

The present invention is concerned with the utilization of tubers at least more deeply colored than light-fleshed tubers in the family Convolvulaceae, including yellow and orange varieties, and including regardless of color, varieties with firm flesh and varieties with moist flesh, with the purpose of producing various flours from the tubers and other valuable edible products and industrial products.

The present invention is concerned with the utilization of orange sweet potato tubers in the family Convolvulaceae, with the purpose of producing various flours from the tubers and other valuable edible products and industrial products.

(2) Description of The Background

Products of dried orange sweet potatoes are well known, and have been reported in the patent literature as early as the 1840's. Dried, ground orange sweet potatoes were patented for use as an ingredient in a coffee blend (U.S. Pat. No. 100,587 issued in 1870) because these dried orange sweet potatoes look and taste like burned bricks. The caroteen pigment seems to have concentrated during drying and to have caused a disagreeable taste and color. The other patented uses of orange sweet potato flour are limited primarily to that of rehydratable powders primarily for use in orange sweet potato pie or pumpkin pies. This is probably due to the strong taste of orange sweet potato flours of the prior art and the fact that when rehydrated, these orange sweet potato flours lose cohesion, and will not keep a shape or hold trapped air.

Uncooked orange sweet potato flour made by the methods of Marshall (U.S. Pat. No.77.995), and Baylor (U.S. Pat. No. 100,587) produced a flour considered inferior. The orange sweet potatoes tended to darken during dehydration; this darkened flour could not be rehydrated to make a good tasting substitute for the original fresh product, and the flour tended to have a very strong bitter taste, particularly when produced by the method of Baylor. Because of the inferior properties of uncooked orange sweet potato flour, in the late 1800's and early 1900's the field as a whole turned emphasis away from uncooked to cooked orange sweet potato flours. In the only mention of uncooked orange sweet potato flour since then, it is described as cattle fodder by Ware (Possibilities in New and Extended Uses of the Sweet Potato, Alabama Agricultural Experiment Station, 9 p., 1941).

Until the instant invention, no orange sweet potato flour, whether uncooked or cooked, has been able to be used as a substitute for more than about 30% of a wheat dough without significant deterioration in texture risen structure, and taste. Even when a 15-85 mixture, by weight, of orange sweet potato flour and wheat flour was used, the resulting bread product was significantly lower in specific volume. At ratios of 20-80 by weight of orange sweet potato flour and wheat flour, the specific volume of the bread product was reduced by about 50 percent.

Other investigators have added cooked orange sweet potato flour to many products such as cookies, cakes, candies, ice cream, breads, and the like. In not one case was it possible to develop a product with orange sweet potato flour as the primary ingredient. It was only possible to add small amounts of cooked orange sweet potato flour to existing recipes containing conventional ingredients. The result was to produce previously known products having orange sweet potato flavor and color.

In my early research on sweet potatoes I tried making and using flours of orange sweet potatoes. The color of the flour was very dark, and the flavor of the uncooked orange sweet potato flour was very strong, as was described by other investigators. When I tried to use the flour to prepare pancakes and the like, the products fell apart in much the same way that fresh orange sweet potatoes tend to fall apart when they are cooked. In agreement with the teachings of the art. I was unable to prepare any products from orange sweet potato flour alone.

I then began to work with white sweet potatoes. In my early research on white sweet potato flour, the white sweet potato flour was made by a high speed impact grinding method which produced a flour of wide particle-size distribution, with the fibrous portions of the tuber remaining in the larger particle sizes, and rendering the flour unsuitably heavy and gritty. When screened. (as is accepted practice in the art to obtain a fine flour) the larger particles (representing about ½ or more of the total weight of the comminuted meal) were removed; this produced a lighter and less gritty flour, but one poorly suited for producing breads and other products where consistency and lightness are important. Applicant found that by eliminating the high impact grinding method, a more uniformly fine flour which incorporated a greater proportion of the plant fiber into the flour was produced, thus greatly improving the ability of the doughs to hold a rise and produce consistently uniform products.

In addition white sweet potato flour was made by soaking white sweet potato tubers in water between the peeling and drying steps. This produced shreds with a high moisture content that made them susceptible to spoilage during dehydration and produced sour-tasting inferior products that spoiled easily. It was found that the soaking step could be eliminated thus eliminating spoilage problems during drying steps and producing a flour of better taste. lower moisture content, and better baking properties.

I then developed a new process for preparing white sweet potato flour which involved reducing moisture content, incorporating more fibrous and other non-farinaceous material into the flour, and obtaining a whole, moderately fine or finer flour. This flour had improved storage capability and provided products of palatable consistency. This white sweet potato flour was suitable for use in baked and other products, and it was possible to develop new processes. different from conventions of the art, which made it possible to use the white sweet potato flour of the instant invention to prepare products with properties and characteristics previously only obtainable from products containing wheat and other grains, legumes, eggs, milk, nuts and the like.

I continued to work with white sweet potatoes exclusively, and developed improved processes. I found that flours retaining most of the substance of the tuber or sweet potato, preferably substantially all of the substance of the tuber or sweet potato, most preferably all of the substance of the tuber or sweet potato, provided a flour with improved properties.

Similarly, I found that including most of the flesh and fiber of the tuber or sweet potato, preferably including substantially all of the flesh and fiber of the tuber or sweet potato, most preferably including all of the flesh and fiber of the tuber or sweet potato, provided a flour with improved properties.

Similarly, I found that flours which in addition to containing starch retain most of the non-farinaceous substance of the tuber or sweet potato preferably in addition to containing starch retain substantially all of the nonfarinaceous substance of the tuber or sweet potato, most preferably in addition to containing starch retain all of the non-farinaceous substance of the tuber or sweet potato, provided a flour with improved properties.

Similarly, I found that flours retaining most of the starch, insoluble substance, and soluble substance of the tuber or sweet potato, preferably retaining substantially all of the starch, insoluble substance, and soluble substance of the tuber or sweet potato, most preferably retaining all of the starch, insoluble substance, and soluble substance of the tuber or sweet potato, provided a flour with improved properties.

The term 'farinaceous' means starch or starchy. In this application, Applicant uses the term 'non-farinaceous' to refer to the components of the tuber other than starch. such as protein, soluble and insoluble fractions, fat, vitamins, minerals, and metabolic products. In the context of a flour or dried product, water will necessarily have to be removed, and some volatiles may be lost during drying. The term 'non-farinaceous' is used to refer to all components other than starch of a whole, dried tuber.

I further found that obtaining this flour by methods which produced a flour without sifting or with very little sifting provided a flour with improved properties.

Thus I found that a dry, whole flour of white sweet potatoes provided a flour with unique properties not obtained before, and one which without the addition of other flours, chemical modifiers, dough strenghtheners, or other foods such as milk, legumes, eggs, sugar, and yeast, could be used to prepare baked products of risen structure that were previously not possible. In other words. the flour alone with no other additives can be used to prepare a dough capable of holding a rise, and is suitable for preparation of baked products of risen structure that were previously not possible.

This is not the orange sweet potato flour with which I began my research. The early flour had been prepared according to the conventions of the art, which included a soaking step, incurring large losses (primarily of soluble and insoluble fiber) due to removal of thick peels, drying at high enough temperatures to provide for carmelization and charring of portions of the sweet potato, obtaining a fine flour by processes of repeated sifting which resulted in the loss again of fibrous material.

After defining the properties for obtaining flour from white sweet potatoes, I began to wonder whether the properties thus obtained would be sufficient to overcome the more hygroscopic nature of orange sweet potatoes, their tendency to carmelize, and the lack of structure upon combining with water.

I therefore prepared a flour of orange sweet potatoes by the method used to obtain the white sweet potato flour, and used the flour in processes for baking bread and other products. To my surprise I found that the flour was not the color of bricks but rather was a very light orange color, did not have the flavor of burned bricks but rather had a very pleasant, slightly sweet, sweet potato flavor. I found that when I used the flour to prepare a bread, the identical proportions and steps described for white sweet potato flour also produced a wonderful-tasting orange sweet potato bread. The risen structure of the bread was at least equal to that of the white sweet potato bread and possibly was slightly higher than that of white sweet potato bread. The color was definitely a bright orange, and the flavor was definitely that of sweet potato; however, without any other ingredients (eg the sugars and spices so often used) the flavor of the bread was very pleasant and satisfying without being overpowering.

In my subsequent research, I have found that contrary to my own teachings, I have been able to obtain a flour from orange sweet potatoes with properties that are sufficient to provide a risen structure to baked products without the addition of any agents for dough strenghthening, without chemical modifiers. and without any added ingredients such as wheat or other grains, eggs, legumes, milk, fat, yeast, or the like.

This orange sweet potato flour, like that for white and light-fleshed sweet potato flours can be used as a complete substitute for milk, eggs, wheat and other grains, legumes, sugar, and the like. I have found that the processes developed for white sweet potatoes and light-fleshed sweet potato varieties provide products of equal properties when orange sweet potatoes are used in these processes. The proportions and processes are generally the same. Thus the methods for making flour and the processes for obtaining a wide variety of products are equally applicable to all types of sweet potatoes and other tubers in the morning glory family, Convolvulaceae, independent of color, and independent of firmness or moistness of flesh.

SUMMARY OF THE PREFERRED EMBODIMENTS

It is one object of the present invention to provide flours and advantageous processes for producing flours from tubers in the family Convolvulaceae.

Another object of the present invention is to provide flours and advantageous processes for producing flours from tubers including those at least more deeply colored than light-fleshed tubers in the family Convolvulaceae, including yellow and orange varieties, and including regardless of color, varieties with firm flesh and varieties with moist flesh, in the family Convolvulaceae.

Another object of the present invention to is provide flours and advantageous processes for producing flours from orange sweet potatoes, in the family Convolvulaceae.

Another object of the present invention is to provide advantageous processes of producing valuable edible products from the flours of all tubers in the family Convolvulaceae.

Another object of the present invention is to provide edible compositions of matter from the flour of all tubers of family, Convolvulaceae.

Another object of the present invention is to provide advantageous processes for producing substitutes for milk, milk-products, and milk containing products.

Still another object of the present invention is to provide advantageous processes for producing substitutes for products containing eggs.

Still another object of the present invention is to provide advantageous processes for producing substitutes for legumes and legume-containing products.

Another object of the present invention is to provide advantageous processes for producing substitutes for nut butter products and products containing nut butters.

Another object of the present invention is to provide advantageous processes for producing substitutes for wheat, other grains, legumes, eggs, milk, and yeast-containing products using sweet potato flour as essentially the only ingredient.

Still another object of the present invention is to provide novel and advantageous processes for producing the following products with sweet potato flour as the only ingredient other than ingredients selected from water, oil. salt, and leavening agent: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, ice cream, milk shakes, puddings, custards, light and heavy creams, condensed milk, muffins, waffles, french toast, crepes, sweet potato pie, and dry mixes for many products.

Another object of the present invention is to provide novel and advantageous processes for producing the following products with sweet potato flour as a primary ingredient: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, ice cream, milk shake, puddings, custards, light and heavy creams, condensed milk. muffins, waffles, french toast, protein coating batter, crepes, sweet potato pie, and dry mixes for many products.

Another object of the present invention is to provide advantageous processes for producing infant formulas.

Another object of the present invention is to provide advantageous processes for producing pharmaceutical products that are more effective for allergy patients by the use of hypoallergenic flours such as sweet potato flour as inert ingredients.

Another object of the present invention is to provide advantageous processes for producing cosmetics containing sweet potato powder as cosmetic base and facial powder, and other uses.

Briefly, these objects and other objects of the present invention as hereinafter will become more readily apparent can be attained by a plurality of method embodiments which employ a flour obtained from tubers of family Convolvulaceae to prepare a variety of different foodstuffs.

Throughout this application, the words 'orange sweet potato' will refer to the sweet potato tubers at least more deeply colored than light-fleshed tubers, including yellow and orange sweet potatoes and including varieties with firm flesh and varieties with moist flesh in the family Convolvulaceae.

Throughout this application, the words 'sweet potato' will refer to all tubers in the family Convolvulaceae including white sweet potatoes, including tubers with light-colored flesh, including tubers that are at least more deeply colored than light-fleshed tubers, including yellow and orange varieties, and including regardless of color varieties with firm flesh and varieties with moist flesh.

Throughout this application, water is repeatedly listed as the liquid ingredient. This is primarily due to the fact that the recipes and processes were developed to be acceptable to the greatest number of individuals suffering from extensive food allergies. Using water instead of milk, for instance, helps insure that milk sensitive persons can use the sweet potato products. The use of water was for hypoallergenic purposes only. Applicant has found that any desired combination of water and substitutes for water may be used in the present invention. Throughout this application, the term 'water' refers to all liquid ingredients or combination of liquid ingredients conventional to the art.

Throughout this application, all statements regarding particle size are such that the particle passes through a mesh opening of a given size. For example, a particle size of 0.015 in mesh, is a particle that passes through a screen mesh opening of 0.015 inch, unless as otherwise noted.

Throughout this application, various particle sizes and types of flours are defined as follows unless otherwise noted: A coarse flour or meal is a flour in which substantially all of the particles range in size from 0.3 inch to 0.02 inch, a moderately fine flour or powder is a flour in which substantially all of the flour passes through a screen with openings of 0.015 inch. a fine flour or powder is a flour in which substantially all of the flour passes through a screen with openings of 0.005 inch, a very fine or ultrafine flour or powder is a flour in which substantially all of the flour passes through a screen with openings of 0.029 inch, and a superfine flour or powder is a flour in which substantially all of the flour passes through a screen with openings of 0.001 inch.

All of the percentages, proportions, and ratios in this application are by weight unless otherwise noted.

Throughout this specification, the terms 'leavening agent' or 'conventional leavening agents' are intended to refer to conventional baking powders, leavening agents such as sweet potato baking powder that would be specifically appropriate for hypoallergenic uses, any other leavening agent of the art, including baking sodas, cream of tartar, other chemical leavening agents (whether wet or dry) yeast-type leavening agents and other means of gas incorporation conventional to the art including but not limited to incorporation of dry ice, and air injection systems with or without pressure.

A sweet potato baking powder is a baking powder in which the active ingredients, for example sodium bicarbonate and calcium acid phosphate, are diluted by a flour of tubers of family Convolvulaceae, including sweet potato flour. In these baking powders, the sweet potato flour has replaced in generally the same proportions. the more standard flours which are generally used as bases for baking powders, such as corn starch or potato starch. Orange sweet potato flours and white sweet potato flours are similarly used in orange sweet potato baking powder and white sweet potato baking powder.

Throughout this specification, any reference to specific baking powders such as sweet potato baking powder or orange sweet potato baking powder is also intended to refer to any other leavening agent of the art, including conventional baking powders, baking sodas, cream of tartar, other chemical leavening agents (whether wet or dry), yeast-type leavening agents, and other means of gas incorporation including including but not limited to incorporation of dry ice, and air injection systems with or without pressure.

Throughout this application the term 'oil' is used to refer to any desired oil or source of edible fat. Very little in the way of adjustment is required to select from among the many oils or fat sources available. Oils which are strongly flavored may provide the predominant flavor o& a finished product, however. Other fat sources such as shortenings and animal fats are also included in the definition.

DETAILED DESCRIPTION OF THE PREFERRED EMBODIMENTS

It has now been found that a flour from tubers of family Convolvulaceae, including orange sweet potatoes, that is useful in the production of many food products can be made. Moreover the flour can be used in every way wheat flour is used, although the processes are different.

In the preferred embodiment, tubers of family Convolvulaceae, including sweet potatoes are subjected to processing which tends not to remove, or minimizes removal of, any of the starch, soluble substances, and insoluble substances of the tubers. Therefore, even though the tubers can be subjected to any preprocessing steps of washing, scrubbing, cutting, rinsing, peeling and the like of the art, it should be accomplished such that the foregoing object is obtained. Very thin peeling (which removes only the outermost layers of the tuber) while water is passing over the tubers is preferred. Although sweet potatoes may also be processed unpeeled and with or without simultaneous washing and peeling, and with or without rinsing (in distilled water is preferred although may be omitted), and may be comminuted, sliced, chopped, shredded, or subjected to any other technique desired for size reduction; methods used by Applicant include simultaneous peeling and rinsing in water and shredding.

Drying the material may be accomplished by methods which tend not to remove, or minimize removal of, any of the starch, soluble substances, and insoluble substances of the tubers. Therefore, even though the tubers can be subjected to any drying steps such as air drying (at any appropriate temperature that avoids carmelization), freeze drying, vacuum drying or any other technique or combination of techniques of the art, it should be accomplished such that the foregoing object is obtained. The dried product provides a moisture content of less than 20%, preferrably less than 15%, more preferably less than 5%, and most preferably equal to or less than 2%.

Reduction to a flour may be accomplished by any technique of the art that tends not to remove, or minimize removal of, any of the starch, soluble substances, and insoluble substances of the tubers. Thus particle size reduction (eg. milling) should be accomplished by methods that (in combination with the prior steps) provide a flour that incorporates 50% or more of the soluble and insoluble substance (as well as starch), up to and including 100% of the flesh and fiber of the tuber in other words, incorporates the entire tuber into the flour or other products produced.

It is recognized that many combinations involving washing, peeling, comminuting, drying, milling and the like are possible, eg drying and particle size reduction may be accomplished simultaneously.

In pulverizing and comminuting steps, desired particle size is achieved while retaining most and up to all of the plant fiber and other non-farinaceous substance of the tuber, that is, in addition to starch, both soluble and insoluble components are retained. Preferably the flour product contains at least 50% of the plant fiber and other non-farinaceous substance of the tuber, more preferably the flour product contains at least 75% of the plant fiber and other non-farinaceous substance of the tuber still more preferably the flour product contains at least 90% of the plant fiber and other non-farinaceous substance of the tuber, still more preferably the flour product contains substantially all of the plant fiber and other non-farinaceous substance of the tuber, and most preferably the flour product contains all of the plant fiber and other non-farinaceous substance of the tuber.

Regarding particle size, in general, as particle size is reduced, the surprising properties of the instant invention are increased; however, these properties can be observed to a lesser degree at larger particle sizes provided that methods have been used which tend not to remove, or minimize removal of, any of the starch, soluble substances, and insoluble substances of the tubers.

Particle size for flours may be selected as appropriate for desired use with particle size selected from coarse flour (in which substantially all of the particles range in size from 0.3 inch to 0.02 inch), moderately fine flour or powder (in which substantially all of the flour passes through a screen with openings of 0.015 inch). fine flour or powder (in which substantially all of the flour passes through a screen with openings of 0.005 inch), ultrafine flour or powder (in which substantially all of the flour passes through a screen with openings of 0.029 inch), and superfine flour or powder (in which substantially all of the flour passes through a screen with openings of 0.001 inch).

Thus the instant flour is comminuted to a size such that substantially all of the flour passes through a screen with openings of 0.02 in, more preferably passes through a screen with openings of 0.015 in, still more preferably passes through a screen with openings of 0.005 in, still more preferably passes through a screen with openings of 0.029 in, and passes through a screen with openings of 0.001 inch.

Dry uncooked tubers of family Convolvulaceae including orange sweet potatoes may be processed to flour material. Thus, in one flour embodiment, dried peeled or unpeeled tubers are preferably thinly peeled, comminuted to a moderately fine to superfine flour by any conventional means, preferably a particle size of 0.015 inch and less, that retains in addition to starch, most of the soluble and insoluble substance of the tuber.

In yet another embodiment the above process is repeated with the added step of partial or complete cooking of the sweet potato by steam heating, boiling, baking or any other desired means, steam heating is preferred, either severally, prior to, or in combination with, drying steps or any other step or steps in the process to produce a cooked or partially cooked flour product.

The above flours may be used in many processes to produce desirable products.

A cereal substance or constituent of cereal may be prepared from the dried shreds or particles of any shape of the sweet potato tuber which are roasted, baked. toasted (with or without oil) by any desired conventional technique.

A particulate material which is useful as a cereal substitute for the likes of cream of wheat can be prepared by comminuting dried tubers of family Convolvulaceae, including orange sweet potato tubers to particle sizes ranging from 0.3 inch to 0.02 inch, preferably 0.06 inch. The tuber may be peeled or unpeeled before processing: peeled tubers are preferred.

A bread product can be prepared from flour of tubers of family Convolvulaceae, including orange sweet potato flour, water, and a small amount of salt (optional), oil (optional). and any conventional leavening agent in proportions ranging from 1:½ to 1:4 by weight, of flour and water, preferably 1:1.4 in processes of mixing at any desired speed, preferably a moderately high speed shaping and baking in any desired order or combinations of techniques common to the art. The sweet potato bread is baked at temperatures ranging from 275-550 ° F. preferably 425 ° F. for 15-90 minutes, preferably 50 minutes. The bread may also be prepared with any desired combinations of conventional ingredients including but not limited to other flours, extenders, binders, fillers, preserving agents, sweeteners, flavorings, seasonings, eggs, milk, nuts, and so forth.

In still another embodiment the bread product described above, and products such as corn bread, cookies, pancakes, muffins, and the like described in examples which follow may be used to prepare bread crumb and crouton-type and other similar products. Breads and the other products, in processes including but not limited to various orders and combinations of drying, toasting, coating, cutting, slicing, comminuting, and the like in steps conventional to the art may be used to produce bread crumb products with all possible uses of any other bread crumb products. These uses include but are not limited to: coating mixes for use alone or with batters, salad toppings, pie crusts, stuffings, and the like. They may also be prepared with any desired combinations of conventional ingredients including but not limited to other flours, extenders, binders, fillers, preserving agents, sweeteners, flavorings, seasonings, eggs, milk, nuts, and so forth.

By techniques in any desired order or combination of slicing, drying. roasting, toasting, baking, and the like, cubed products called croutons may be produced. These may be used on salads soups, stews, stuffings, and any other ways croutons are used. The bread crumbs and croutons may also be prepared with any desired combinations of conventional ingredients including but not limited to other flours, extenders, binders, fillers, preserving agents, sweeteners, flavorings, seasonings, eggs, milk, nuts, and so forth.

In another embodiment, a corn bread-like product can be prepared from sweet potato flour, water, oil, and small amounts of salt (optional) sweeteners (optional). and any conventional leavening agent in proportions of flour, water and oil ranging from 1:6:⅓ to 1:1/2:0, by weight. preferably 1:1.5:1/24 with processes of mixing at any desired speed, preferably a moderately high speed, shaping, and baking in any desired order or combinations of techniques common to the art. The sweet potato corn bread is baked at temperatures ranging from 275–550 ° F. preferably 425 ° F., for 15-90 minutes, preferably 50 minutes. When a liquid sweetener such as a honey is used, the proportions range from 1:6:2:1/3 to 1:1/2:0:0, preferably 1:1.2:0.2:0.04 of sweet potato flour, water, honey, and oil. The corn breadlike product may also be prepared with any desired combinations of conventional ingredients including but not limited to other flours, extenders, binders, fillers. preserving agents, sweeteners, flavorings, seasonings, eggs, milk, nuts, and so forth.

In another embodiment, a cake dough product can be prepared, in the method described above for corn bread by increasing ranges and preferred amounts: the amount of oil by 100%. increasing the amount of honey by 20%, and increasing the amount of baking powder by 25-50%. Alternatively, honey may be omitted. These doughs produce a baked cake-like product without added ingredients, although ingredients commonly used in the art may also be incorporated into the dough or added to the finished products. The cake may also be prepared with any desired combinations of conventional ingredients including but not limited to other flours, extenders, binders, fillers, preserving agents. sweeteners, flavorings, seasonings, eggs, milk, nuts, and so forth.

In still another embodiment by the processes described for corn bread products, muffins may be produced. The range of ratios of flour water, and oil are the same as for the corn bread product with preferred proportions of 1:1.3:1/24.

In another embodiment, products the likes of pancakes, doughnuts, hush puppies, batter, crepes, dumplings, and waffles can be prepared from combinations of sweet potato flour, water, oil, and small amounts of salt (optional), sweeteners (optional), and of any conventional leavening agents in proportions virtually identical to those for corn bread. The ranges of general proportions are identical with preferred proportions being 1:1.5:1/12. These products are mixed, molded, shaped, fried, and so forth as appropriate for the product. The pancakes, doughnuts, hush puppies, batter, crepes, dumplings. and waffles may also be prepared with any desired combinations of conventional ingredients including but not limited to other flours, extenders, binders. fillers, preserving agents, sweeteners, flavorings, seasonings, eggs, milk. nuts, and so forth.

In still another embodiment the above described pancake batter prepared as described earlier may be used as a pizza dough. In processes involving pouring the batter onto an appropriately shaped or sufficiently large surface, heating or baking in temperatures ranging from 375–525 ° F. preferably 425 ° F. until the dough is almost done but still tacky on the top, about 10–30 minutes, preferably. Add any desired ingredients including but not limited to various meats, cheeses, vegetables, spices, and other materials common to the art. Although any ingredients may be used, hypoallergenic ingredients might include ground precooked venison and nopales. Bake until dough is completely done and ingredients thoroughly cooked, about 6–20 minutes.

Alternatively, the toppings described above may be placed on the batter before cooking begins. Alternatively, the above dough may be thoroughly baked. toppings added, and pizza reheated. Alternatively the dough described for pie crust may be used as a pizza dough. The dough is prepared as described in the example, the dough is rolled out to the desired length, width, and thickness. toppings of any kind are added and the mixture is baked at 350 ° F. for 10–30 minutes.

In another embodiment, a product such as french toast batter can be prepared from sweet potato flour, water, oil, uncooked, proteinaceous material, and a small amount of salt (optional) in proportions ranging from 5:12:8:8 to 1/10:12:0:0 by weight, preferably 1:12:2:2 in processes of gelatinizing the flour and water mixture combining with remaining ingredients and blending until smooth and homogenous. Material to be coated and prepared for french toast is preferably sweet potato bread, although any other bread or bread-like product may be used, and cooking is by any accepted technique. Alternatively batter may be prepared by the method above omitting the step of gelatinizing the flour-water mixture.

Alternatively the proteinaceous material may be omitted, with the above proportions of flour and water remaining unchanged. The batter may be used alone, or in combinations with bread crumbs and any other coating materials. The batter may also be prepared with any desired combinations of conventional ingredients including but not limited to other flours extenders, binders, fillers, preserving agents, sweeteners, flavorings seasonings, eggs, milk, nuts, and so forth.

In another embodiment, a product such as cookies can be prepared from sweet potato flour, water, oil, small amounts of salt (optional). sweeteners (optional). and small amounts of any conventional leavening agents in proportions ranging from 4:1:0 to 0.5:1:2, by weight, preferably 1.8:1:0.9 in processes of mixing, kneading, shaping, baking to produce cookies. Baking conditions range from 275–500° F. preferably 350° F. and 2–40 minutes preferably 8–10 minutes.

Alternatively, when a liquid sweetener is used, the proportions are within the ranges described above, preferably 1:1.5:0.3 and 0.24 parts honey or other liquid sweetener per 1 part flour. Sweetener amounts may range from 0–1 part per 1 part flour.

Alternatively, add toppings as desired to the unbaked or baked dough. Any desired fruit nuts, flavors, seasonings, sweeteners of the conventional art may be incorporated. The cookies may also be prepared with any desired combinations of conventional ingredients including but not limited to other flours, extenders. binders, fillers, preserving agents, sweeteners, flavorings, seasonings, eggs, milk, nuts, and so forth.

In yet another embodiment, crackers may be produced in any suitable machine for mixing doughs through processes involving combining flour, water, and oil in proportions ranging from 3:1:4 to ½:1:0, preferably 1:1:1/6 parts flour, water, and oil and small amounts of salt and leavening agents. In processes including but not limited to molding, rolling, cutting, and extruding, shape dough into desired cracker shapes. Dough may or may not be coated with a thin film of oil and salt. Any conventional heating method may be used preferably 50° F. for 20 minutes. The crackers may also be prepared with any desired combinations of conventional ingredients including but not limited to other flours, extenders, binders, fillers preserving agents, sweeteners, flavorings, seasonings, eggs, milk, nuts, and so forth.

In another embodiment of the invention a product such as tortillas or chips can be prepared by blending sweet potato flour with water, and then baking or frying the appropriately shaped dough. In preparing the mixture a range from ½:1 to 2:1 amounts of flour and water are blended, preferably 0.9:1 flour and water. Any way that tortillas and chips are made in the prior art may be used in the present invention.

In still another embodiment of the invention, a food product such as pie crust is prepared by blending flour, water, and oil in ratios of 1:0.4–1.5:0.1–1, preferably 1:0.7:0.3. Once the blend is prepared, it is kneaded, shaped or molded and baked if desired at temperatures ranging from 275 to 500 ° F., preferably 350° F. for from 2 to 45 minutes, preferably 10 minutes.

In yet another embodiment, doughs from processes described earlier for pie crust and pasta may be used to produce a puffed product by shaping the dough into flat, thin waters and frying the wafers in hot oil to produce a puffed or popped product. The dough may be shaped into a wafer or any other shape desired by combinations of extruding or other shaping means, rolling, cutting and other techniques in any order in any desired combination and fried. By this method shapes of a 'chip' or 'fry' may be obtained. Also long pieces may be shaped into a pretzel-like shapes and fried.

A puffed product may also be obtained when sweet potato flour is combined with pureed, cooked sweet potato. Although almost any desired combination may be used ranging from 5–100% flour, 0–95% cooked and pureed sweet potato, 0–50% water, the ratios for pie crust combined with an added 20% cooked sweet potato is preferred. Either of the above processes may be used to produce very small-sized ¼"–1" wafers, flakes and granules which can be used as a cereal product. Although for hypoallergenic purposes the above is preferred, any combination of flours, other tubers, other powdered vegetable material, extenders, binders, fillers, adhesives, antioxidants, preservatives, sweeteners, flavorants, spices and the like may be used with the above process.

In yet another embodiment of the invention, pretzels may be prepared from the doughs described for tortillas, chips, and pie crusts in processes of shaping optional salting. and various combinations of baking with or without a thin coat of oil, frying, broiling, steaming, drying common in the food art to produce a pretzels of desired sizes and shapes. Additional embodiments include the pretzels above to which have been added to dough before baking or to the outside surface before or after baking, a variety of fillers, extenders, binders, flavorings, seasonings, preservatives and the like common to the art.

In yet another embodiment, the thick dough produced by the processes described in the preparation of pie crust may be used to produce dough encased or wrapped food products. The kneaded, thoroughly mixed dough may be shaped by extruding, rolling, cutting, and any other convenient technique to produce a variety of shapes onto which pureed fruit chopped meats, hot dogs, meat and vegetable combinations, cheese and the like may be placed. For example the thick dough may be shaped into $3 \times 3 \times \frac{1}{4}$ inch squares onto which a pureed fruit such as sapote or carambola, and any other unusual or common fruit, are placed. These may be baked, broiled, or fried as is or 2 squares may be placed together such that the fruit forms a middle or inside layer in a sandwich-type effect. This may be baked, broiled, or fried to produce a product or may be frozen for sale to the consumer as a frozen product.

In another example, conventional art may be used to completely encase fruit or meat and vegetable mixtures. The dough covered product which may have any shape, commonly an ovoid shape ranging from 1 to 6 inches in length may be baked, boiled, broiled, fried and so forth in any conventional means to produce good tasting, convenient foods.

The dough may also be used in the so called pot pie products.

In another example, pureed or flaked meat may be combined with a small amount of imitation mayonnaise in approximate proportions of 2:1 and placed on a $6 \times 6 \times \frac{1}{4}$ inch dough square. The dough is rolled around the meat mixture to form a tamale-like shape. This product may be baked, broiled, fried, or frozen. If uncooked meats are used, the product should be cooked by means other than frying. The dough-wrapped products may also be prepared with any desired combinations of conventional ingredients including but not limited to other flours, extenders, binders, fillers, preserving agents, sweeteners, flavorings, seasonings, eggs, milk, nuts, and so forth.

In another embodiment, sweet potato flour may be combined with a vegetable oil such as sunflower oil, olive oil, or the like in an amount ranging from 1/2:1 to 4:1 parts by weight flour per part oil. preferably 1.8:1 to which is added a gelatinized flour-water mixture which contains flour and water in proportion ranging from 1:1 to 1:30, preferably 1:6 to produce a sweet potato nut butter. The flour/oil mixture and flour/water mixture are combined in amounts by volume ranging from 20:4 to 20:0. preferably 20:1.

Alternatively, the sweet potato nut butter may be obtained by combining sweet potato flour and oil only, in the ratios described above for sweet potato nut butter.

The flour may be combined with various ingredients to prepare a colloidal product having the consistency of mayonnaise. Flour, water, and oil are combined in ratios of 0.5–3:1–15:1–15, preferably in ratios of 1:9.5:5. The flour and $\frac{1}{4}$ to all of the water, preferably all of the water are combined and heated by any convention of the art to such temperature and for sufficient time to completely gelatinize the starch granules. This mixture in steps of cooling (optional) and high speed blending with any remaining water, oil, and starchy tuber to produce a colloidal product to which may be added any acid, such as lemon juice, citric acid, ascorbic acid, acetic acid and the like in amounts ranging from 0–2 parts acid to 1 part original flour used, about 0.6:1 is preferred.

The mayonnaise has the colloidal properties of mayonnaise, with no other added ingredients. This is not to preclude the use of other ingredients commonly used in the food art, including but not limited to eggs, milk, other flours and starches, sweeteners, flavors, seasonings, and spices of any kind.

The mayonnaise produced by the above process has the advantages of being able to be frozen and thawed without destroying or significantly altering the colloidal properties of the product.

In another embodiment of the invention custard-type products may be produced. When flour and water are combined in proportions ranging from 1:1 to 1:30, preferably 1:6. and heated with stirring until gelatinized to a thick paste-like glue and subjected to blending in high speed blending device with the addition of oils in proportions ranging from 0:1 to 3:1, preferably $\frac{1}{2}$ part oil per 1 part original flour by weight, this process produces creamy fluids of various thicknesses with properties similar to evaporated milk, which when allowed to stand with or without cooling, will solidify to produce products with properties very similar to custards. These custard-type products may be used without modifications as custards. In another embodiment the fluids may be combined with vegetables such as peas, corn, and squash to form custards commonly called corn puddings and the like. The fluid may be combined with pureed vegetables such as corn, pumpkin, and squash to produce custard-like pies, and with fruits such as peaches, apricots, coconut, and bananas to form creamed pies and the like.

One of the advantages of these products is that they do not require further cooking to produce the "setting up" and when combined with precooked vegetables, and the like, do not need additional baking or other heat treatments. The custards may also be prepared with any desired combinations of conventional ingredients including but not limited to other flours, extenders, binders, fillers, preserving agents, sweeteners, flavorings, seasonings, eggs, milk, nuts, and so forth, but they are not necessary to achieve the desired product.

In another embodiment of the invention, a product such as a pudding can be prepared by blending flour, water, oil, and pureed fresh sweet potato paste in proportions ranging from 1/7:10:6 to 1/7:1/2:1/10. preferably about 1/7:2:1. The product is produced in processes where as a first process step the flour and from 10 to 100%, preferably 50% of the water are combined and heated by any convention of the art to produce a thick gelatinized paste. This paste is then combined with the remaining uncooked materials and blended to a smooth, homogenous, mixture by conventional mixing techniques. With the addition of no additional ingredients the product has a sweet, pleasant taste. However, this is in no way intended to preclude the use of other constituents commonly used in puddings including but not limited to any desired combinations of conventional ingredients including but not limited to other flours, extenders, binders, fillers, preserving agents, sweeteners, flavorings, seasonings, eggs, milk, nuts, and so forth.

Alternatively, a pudding-type product may be prepared using flour and water only, in proportions ranging from 1:1 to 1:30 preferably 1:6. The ingredients are combined, heated by any conventional techniques until the mixture is completely gelatinized. Cool to between 30–0° C, preferably 10–20 ° C. until the consistency of pudding.

In still another embodiment, in processes as are described for pancakes; flour, water, oil, baking powder, and salt are combined in proportions preferably of 6:11:1:1/2:1/8, but ranging from 8:12:1:1:¼ to 4:5:1:0:0 to produce a crepe-type product. The batter may be used by techniques known to the art when cooking and using the sweet potato batter for crepes. They may also be prepared with any desired combinations of conventional ingredients including but not limited to other flours, extenders, binders, fillers, preserving agents, sweeteners, flavorings, seasonings, eggs, milk, nuts, and so forth.

In still another embodiment of the invention, when a given amount of sweet potato flour is mixed with water of a temperature range from 0 to 150 degrees ° C., 100° C. is preferred, in proportions ranging from ½ to 4 parts of flour per part water, preferably 1⅛ parts flour to one part water, a dough can be prepared, which, after maintaining a heating and kneading period of from 0 to 10 minutes, preferably 1 minute, followed by extruding, cutting and drying, prepares such products as noodles pastas and the like. It is also possible to mix the batter prepared with baked camote or other farinaceous and mealy textured tubers and possibly other vegetable matter in the amounts to produce stiff doughs for gnocci hard dumplings, and other pasta products.

In another embodiment of the invention an egg substitute may be prepared by combining sweet potato flour and water in proportions of 1:2–30 parts flour and water, preferably 1:6 parts flour and water, and heating the combination with stirring to form a thick gelatinized paste.

This egg substitute may be added to the above described dough mixture before extrusion to any desired pasta shapes, to produce substitutes for egg based pasta.

In a further embodiment of the invention, the pasta doughs described above, with or without the egg-substitute may be heated at temperatures above 50° C. for 2–30 minutes, preferably 2–5 minutes at 95° C. to gelatinize a part of all of the dough prior to extrusion.

The pastas thus described are dried by any conventional means, preferably air dried on trays to produce a final product.

In its final uses this pasta does not swell significantly beyond its dried size, when cooked in boiling water and the like. This is due to the fiber content which has been retained in the flour. These fibers prevent the typical swelling and conversion to a jelly-like mass common to noodles from most pure starches. Thus these pasta products retain a form and consistency similar to wheat-based noodle products. They may be used in all ways any other noodles are used.

In another food embodiment the sweet potato flour can be combined with water in a ratio of 12:1 to 3:1 parts by volume water per unit volume of flour, preferably 6:1 water to flour, and a small amount of a vegetable oil to produce a sweet potato milk. Preferably half of the flour and water are combined (actual amounts may range from 10–80% flour and 25–100% water), heated by conventional methods until the mixture is completely gelatinized. The gelatinized mixture and remaining ingredients are combined thoroughly mixed in a high speed blending device to produce a orange sweet potato milk or other similar fluid mixtures.

In the above milk embodiment, flour of almost any particle size may be used ranging from very coarse to superfine. The particle size is not important for that portion of the flour used for gelatinization, although fine flours are preferrable. A more finely divided flour product (ranging from a fine to ultrafine to superfine flour) is desired for the flour that remains uncooked in the milk. The smaller the particle sizes the better preferably at least less than 0.005 inch, most preferably at least less than 0.001 inch. The milk produced from fine to superfine flours does not require straining to yield a smooth homogenous product. Larger particle sizes produce a gritty product that must be strained before use. The larger the particle sizes, the greater proportion of sweet potato flour that is removed by straining, and the more separation into layers that occurs on setting.

In another food embodiment, sweet potato flour can be combined with water in proportions ranging from 1:1 to 30:1 parts by volume of water per unit of flour, preferably 3:1 water to flour for heavier creams and 6:1 for lighter creams, and a small amount of a vegetable oil. Fifty to 100 per cent of the flour is combined, and heated until the mixture is completely gelatinized. The gelatinized mixture and remaining ingredients are combined, thoroughly mixed in a high speed blending device to produce substitutes for light to heavy creams and condensed milk.

In another embodiment of the invention sweet potato flour may be combined with water in amounts from 1:1/2 to 1:6, preferably 1:1.5, a small amount of oil, and crushed ice to prepare milk shake and ice cream-like products. From ¼ to ¾ of the flour, preferably ½ of the flour used is combined with water heated by any convenient means until thoroughly gelatinized, then combined with remaining flour, crushed ice, and a small amount of oil in a suitable blending device to produce a thick milk shake-like slurry product. The sweet potato milk shake has a pleasant taste without further additions, but may also be flavored with any fruits, nuts, sweeteners, or other flavors to produce many flavors and blends. The milk shake product may also be prepared with any desired combinations of conventional ingredients including but not limited to other flours, extenders, binders, fillers, preserving agents, eggs, milk, nuts, and so forth.

In another embodiment the above milk shake-like product may be used in processes of freezing, pulverizing, in one or two freezing and pulverizing cycles, to produce a product blended to a creamy consistency of ice cream. The sweet potato ice cream has a pleasant taste without further additions, but may also be flavored with any fruits, nuts, sweeteners, or other flavors to produce many flavors and blends. The ice cream product may also be prepared with any desired combinations of conventional ingredients including but not limited to other flours, extenders, binders, fillers, preserving agents, eggs, milk, nuts, and so forth. This product may also be used as an ingredient in more conventional ice cream preparations.

In another embodiment, a more creamy ice cream and milk shake product may be produced by increasing the amount of fat or oil in the product.

In other embodiments of the invention, the instant flour may be employed as a thickener, filler, or extender in the preparation of food products. hypoallergenic cosmetics, and industrial products. Examples of industrial uses include use as a filler in various industrial products, as an ingredient in the manufacture of paints, and as an adhesive or in adhesive formulations whose applications include but are not limited to use in various wood glues and in the manufacture of plywoods.

Many individuals are not only allergic or hypersensitive to foods they eat, but also to materials in their surroundings. To find well tolerated products for use in the home, work, and other surroundings, it is desirable to select from well tolerated, hypoallergenic materials, such as the flours of the instant invention; hence uses of the instant flours that include adhesives, paints and coatings.

The flours of the instant invention, together with water, oil (optional), and desired pigments provide a well-tolerated paint and coating suitable for use on interior and exterior surfaces, and furnishings, that provides a durable, long-lasting coating, resistant to flaking and that also has the advantage of being free of indoor air pollutants.

Any added ingredients conventional to the art may also be added to the above embodiment, such as other binders, solvents, resins, polymers, and the like. These will also provide suitable paints and coatings, however, the added ingredients as is presently the case for most paints and coating of the art, may contribute indoor air pollutants, release volatile substances to the environment, and cause reactions in sensitive persons.

Cosmetic preparations may be prepared in manners similar to the prior art to provide products such as face powders, dusting powders, lip sticks, lotions, cosmetic foundations, and liquid and paste makeups. These cosmetics are all used for topical application that is applying to the skin, and are not taken internally. They are applied in a conventional manner, eg, applying the face powder or dusting powder with a puff or other applicator conventional to the art in light amounts to the skin and massaging until smooth and even, applying a lip stick and/or lip gloss to the lips, applying a lotion to the skin and massaging it in, and applying cosmetic foundations, and liquid and paste makeups to the skin by hand or with a suitable applicator and massaging until smooth.

The proportions of orange sweet potato flour can be adjusted so as to give the desired consistency for lotions, thickness for lip sticks and lip balms, and color for all cosmetic preparations.

For example, sweet potato flour of fine to superfine particle sizes may be used in dusting powders and face powders. Various shades may be obtained by heating and toasting methods. This produces a face powder product which could be well tolerated because people would be only placing non-allergenic items on their faces. Similar powders may also be used as bases for liquid and paste makeups to produce hypoallergenic products.

In other words these cosmetic preparations are made in ways conventional to the art with the exception that it contains as an active ingredient, sweet potato flour. The cosmetic preparations may also be prepared with any desired combinations of sweet potato flour with conventional ingredients including but not limited to other flours, extenders, binders, fillers, preserving agents, and so forth. These cosmetic preparations so prepared can be applied and used in the manners conventional to the art.

The cooked sweet potato flour may also be used in combination with the uncooked sweet potato flour in many of the products and processes described previously, and may also be used with many other types of flours.

The earlier described process for producing sweet potato milk may be used to produce infant formulas, in which uncooked or completely or partially cooked sweet potato flour is used. The prior art provides infant formulas in forms such as ready-to-feed, liquid concentrate, and dry powder; the above sweet potato infant formulas provided in forms of the prior art such as ready-to-feed, liquid concentrate, and dry powder are hereby included in the embodiment.

In another embodiment, sweet potato flour may be used in a wide variety of pharmaceutical products for mammals including humans as a hypoallergenic filler, extender, excipient, and inert ingredient. The use of a hypoallergenic material for these purposes would eliminate allergic reactions that food allergic patients may have to the nonactive ingredients, and could help medications to be more effective for the allergic patient.

It is within the scope of this invention to include conventional additives and additional ingredients used in other such products, including but not limited to grain flours and other flours, other flour products, starches, and flours of the instant invention, eggs, milk and milk products, nuts, other fat sources, legumes, fruits, vegetables, extenders, binders, chemical modifiers. fillers, preserving agents, sweeteners including sugar and other conventional sweeteners, flavorings, seasonings, yeast as a leavening agent, and so forth.

It should be noted that the foregoing descriptions of various embodiments are exemplary only, and should not be interpreted as a limitation of the invention. It would be within the skill of the art to optimize by changing proportions depending upon the fineness of the flour, the water content of the flour, and the like.

It is clear that the flour of the present invention may generally be mixed with any other more conventional flours such as wheat, corn, millet, milo, soy, lentil, and the like, and any other non-conventional flours such as arrowroot, water chestnut, artichoke flours, and the like, as well as those disclosed in U.S. Pat. Nos. 4,923,709, 4,911,943, and application Ser. No. 294,690 filed Aug. 1, 1988, application Ser. No. 825,656 filed Jan. 31, 1986 application Ser.825,658 filed Jan. 3, 1986, application Ser. No. 825,659 filed Jan. 31, 1986, and application Ser. No. 825,660 filed Jan. 31, 1986, all of which are incorporated by reference, in processes suitably modified according to the individual characteristics of each flour.

The invention provides novel flavor enhancing properties not heretofore recognized nor obtainable. For example sweet potato flours have been found enhance the flavor of the finished product when sweet potato flours are added to products containing meats, nuts, fruits, vegetables, and sauces. Sweet potato flours are particularly desirable as additives to meats, cookies, muffins, pies and the like.

Another observed benefit of the novel flours, either alone or in a mixture with other foods, is that the products of the instant invention provide the beneficial effects of satisfying hunger and providing a full sensation, and providing sustained energy for several hours without causing hunger or energy peaks and sags. This property provides added benefits when products of the instant invention are used for snack foods foods for athletes, foods for individuals who desire reduced caloric intake and the like. Therefore it is also beneficial to add portions of the flour to other foods so as to obtain the beneficial effects of satisfying hunger and providing a full sensation, and providing sustained energy for several hours without causing hunger, or energy peaks and sags.

Many of the products described above are well suited for the preparation of packaged dry mixes, frozen products and the like.

It is within the scope of this invention to remove some of the naturally occurring fiber and substitute it with fiber from another source. eg. cellulose or another tuber as well as adding additional fiber to that naturally occurring to this invention.

Although I have described a process starting with a whole tuber, it is also within the scope of this invention to obtain the components of whole flours and assemble the components themselves to provide the properties of the whole flour. These components, such as starch, insoluble fiber, eg, cellulose, and soluble substance such as but not limited to mucilages and gums, and dried vegetable juices may be assembled separately from materials obtained from different sources which may then be mixed together. Mixing, such as milling together of such separately obtained sources of ingredients provide the properties of the instant invention.

As is evident from the above discussion, the central objective of the present invention is to provide a variety of different foodstuffs, the basis for all of which are tubers in family Convolvulaceae.

Having generally described this invention, a further understanding can be obtained by reference to certain specific examples which are provided herein for purposes of illustration only and are not intended to be limiting unless otherwise specified.

EXAMPLE NUMBER 1

Orange Sweet Potato Bread

Place 453 g orange sweet potato flour in a suitable conventional mixing device. Slowly add 623 g water and 3.25 g salt while mixing at lowest speed. When well blended mix. at highest speed for about 1 minute. Stir in 47 g baking powder; then mix at high speed for 15 seconds. As fast as possible pour into baking pan. Carefully place in oven heated to 425° F. and bake for 50 minutes. The amount of water needed varies with the moisture content and particle size of the flour. More coarse flour and/or flour with a lower moisture content will require more water. The resultant sweet potato bread product may be used in any way wheat bread is used.

EXAMPLE NUMBER 2

Orange Sweet Potato Imitation Corn Bread

Ingredients: 304.8 g orange sweet potato flour 453 g water, 23.6 g orange sweet potato baking powder. 6.5 g salt, 12.5 g oil. Combine above ingredients with baking powder added last; mix well, at highest speed with conventional mixing equipment until well blended and uniform consistency about 1 minute. Transfer quickly into suitable baking container and bake 20–25 minutes at 425° F.

Alternatively, the following proportions may be used in an imitation corn bread with honey or other liquid sweetener: 343 g orange sweet potato flour, 396.4 g water, 6.5 g salt. 75 g honey. 23.6 g orange sweet potato baking powder, 12.5 g oil.

EXAMPLE NUMBER 3

Orange Sweet Potato Cake Dough

The following ingredients: 343 g orange sweet potato flour, 396.4 g water, 90 g honey, 35 g oil, 35.4 g suitable leavening agent, may be combined in the processes described in Example 2. Dough may be baked as described in Example 2. prior to baking or after the cake dough may be prepared or finished with any desired combinations of conventional ingredients including but not limited to other flours, extenders,. binders, fillers, preserving agents, sweeteners, flavorings, seasonings, eggs, milk, nuts, and so forth.

EXAMPLE NUMBER 4

Orange Sweet Potato Muffins

Combine 343 g orange sweet potato flour, 453 g water, 6.5 g salt, 12.5 g oil, and mix well, at high speed with conventional techniques of the art until smooth and well blended. Add 23.6 g baking powder and mix well. Pour quickly or transfer by other means into suitable baking equipment. Bake for 20–25 minutes at 425° F.

EXAMPLE NUMBER 5

Orange Sweet Potato Pancakes

The following ingredients: 304.8 g orange sweet potato flour, 453 g water, 6.5 g salt. 50 g oil. 23.6 g orange sweet potato baking powder, are combined and mixed well on highest speed, preferably 1–2 minutes in high speed blending device. Batter may be transferred to suitable baking or frying device, device to be prepared as required by the art,. preheated on medium-high heat. Dough may be cooked in sizes ranging from dot sizes to several feet across. Turn when top surface has turned dull and the bottom surface is golden brown in color.

When honey or other liquid sweetener is used, the ingredients: 304.8 g orange sweet potato flour, 453 g water. 6.5 g salt, 75 g honey, 50 g oil, 23.6 g sweet potato baking powder,. may be used in the process described above.

EXAMPLE NUMBER 6

Orange Sweet Potato Pancake Mix

To provide an example of a dry mix-type product, orange sweet potato pancake mix is used. A orange sweet potato pancake mix product can be made by combining ingredients: 453 g flour, 8.7 g salt, and 10.7 g orange sweet potato baking powder. Mix ingredients well in a rolling ball mill or other conventional means to form a dry mix. Pancakes can be made from this dry mix by the addition of water and water/oil mixtures.

Alternatively, by conventions of the art the pancake mix oils may also be added to the above ingredient mix to produce a dry mix that contains oils. Also, sweeteners, flavors, seasonings, binders, fillers, and so forth may be utilized in the production of sweet potato pancake mixes.

EXAMPLE NUMBER 7

Orange Sweet Potato Pizza Dough

The batters described in Example 5 may also be used as a pizza dough. Prepare batter as described above, pour dough onto pizza pan. Place in oven and bake at 425 degrees until dough is almost done but still tacky on the top. about 20 minutes. Add any desired ingredients, various meats, vegetables, spices, and other materials common to the art. Bake until dough is completely done and ingredients thoroughly cooked,. about 10 minutes.

Alternatively, the topping can be placed on the batter before cooking begins, or after cooking ends. Alternatively, the dough described for pie crust, Example 15. may be used as a pizza dough. The dough is prepared as described in the example, the dough is rolled out to the desired length, width, and thickness, toppings of any kind are added and the mixture is baked at 350° F. for 10–30 minutes.

EXAMPLE NUMBER 8

Orange Sweet Potato Waffles

The following ingredients are combined by the method described above in Example 5: 304.8 g orange sweet potato flour 509.6 g water, 6.5 g salt, 50 g oil, 23.6 g orange sweet potato baking powder. Pour batter into waffle iron or other suitable molding or shaping device preheated to 300-500° F. Watch for steam coming from the waffle iron as the waffles cook. Leave waffle iron closed as long as steam can be seen rising from the waffle iron. When steam stops, all water has been baked out of the batter and waffles are done, 5-10 minutes or more. When done the waffles should be golden brown in color.

EXAMPLE NUMBER 9

Orange Sweet Potato French Toast

Combine 19.5 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely pulverized and liquefied or combine 19.5 g flour and 226.5 g water. Heat by any desired convention until mixture is well gelatinized and thickened. Let cool.

Coat pieces of orange sweet potato bread. Fry to slightly browned and crusty in lightly greased griddle or skillet preheated to medium high. Alternatively french toast batter may be prepared by the method as described above without cooking the flour/water mixture.

French toast batter may be used for many combinations with sweet potato bread crumbs and many other coating materials or alone.

EXAMPLE NUMBER 10

Orange Sweet Potato Cookies

Combine and mix well by the conventional art: 304.8 g orange sweet potato flour. 170 g water. 6.5 g salt. 150 g oil. 12 g sweet potato baking powder. Form into cookie shapes by the conventional art. Bake at 350° F. on ungreased surface for 8-10 minutes, or until a light golden brown on the underside. Alternatively, add toppings as desired to the unbaked or baked dough. Any desired fruit, nut, flavors, seasonings of the conventional art may also be used.

When a liquid sweetener or honey is used, the following ingredients are combined as described above: 304.8 g orange sweet potato flour 453 g water, 6.5 g salt 75 g honey, 100 g oil, 12 g sweet potato baking powder.

EXAMPLE NUMBER 11

Orange Sweet Potato Doughnuts, Pretzels, Hush Puppies, Doughnut Holes

From batter prepared in the method of Example 5, extrude batter through a doughnut press or any other desired device in rings onto hot oil; batter may also be dropped in balls, long pieces, even pretzel shapes. Temperature of the oil should be about 300–500 degrees.

If the oil is hot enough the dough will float at the top of the oil. Fry doughnuts or other shapes until golden brown on all sides. Remove from oil drain. Serve plain or top with fruit, honey, nuts, coconut, peanut butter, and the like.

Alternatively, doughnuts may be preparations of conventional ingredients including but not limited to: other flours, extenders, binders, fillers. preserving agents. flavorings, seasonings, eggs, milk, and so forth.

EXAMPLE NUMBER 12

Orange Sweet Potato Dumplings

Combine 152.4 g orange sweet potato flour 226.5 g water, 4.9 g salt, 12 g sweet potato baking powder until smooth and creamy. Let dough set for about 15 minutes. Drop teaspoon-sized portions of batter into about 2 liters of rapidly boiling water or broth, may be thickened. Allow to remain in boiling water 2-6 minutes, preferably 5 minutes. If dumplings remain in boiling broth longer. dumplings will dissolve. When done, dumplings will be light and tender on the inside.

EXAMPLE NUMBER 13

Orange Sweet Potato Batter

A batter prepared by the method of Example 5 may be used as batter for deep frying and for fondue cooking techniques. Coat vegetables fruit, or cooked meat in batter and deep fry in hot oil (preheated to medium-high heat). If the oil is hot enough the dough should float at the top of the oil. Test for proper temperature with a small ball of dough.

EXAMPLE NUMBER 14

Orange Sweet Potato Crepes

In yet another embodiment of the batter prepared in Example 5, the batter may be used to make a crepe-like product. The batter may be diluted by the addition of 10–400 g water, preferably 100 g to make a crepe-like product. The batter is spread in very thin layers on a cooking surface, and prepared according to the accepted convention.

EXAMPLE NUMBER 15

Orange Sweet Potato Pie Crust

Mix thoroughly, 152.4 g orange sweet potato flour, 50 g oil, 113.25 g boiling water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery.

Orange sweet potato pie crust may be used as a double or single crust pie, with any type of filling, including meat (eg, chicken pot pie) or fruit filling. May be used baked or unbaked. For a baked pie crust, bake for 10 minutes at 350° F.

Although above ingredients are preferred, orange sweet potato flour may be used with shortening or lard and any other conventional ingredients. For example, when using lard, use about 100 g and decrease water to 10–14 g. Dough will seem stiff and hard, but will be just right after baking.

EXAMPLE NUMBER 16

Orange Sweet Potato Tortillas, Chips

Mix 152.4 g orange sweet potato flour with 170 g water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 17

Orange Sweet Potato Pretzels

Doughs produced by the processes described in Examples 15 and 16 may be used in processes of shaping to form pretzels of various sizes, coating with oil (optional), cooking by various processes of the art including but not limited to baking, frying, and drying to produce pretzels of varying sizes.

In alternative processes, pretzels may be produced in processes above into which are incorporated any combinations of processes including but not limited to additional flours, eggs, milk, flavorings, seasonings, binders, fillers, extenders, and preserving agents.

EXAMPLE 18

Orange Sweet Potato Imitation Nut Butter 453 grams of orange sweet potato flour are placed into any blending equipment suitable for mixing very thick doughs at very high speeds, to which is added 200–250 g edible fatty material, such as vegetable oils (preferred for hypoallergenic products) but could also include other fatty materials add to this a paste made of 4.7 g flour 28.4 g water that has been cooked. The materials are intimately mixed for about 2 minutes or until the entire mixture is well blended, and the consistency of peanut butter.

Alternatively, the nut butter substitute can be made by the flour and oil mixture alone, omitting the flour and water paste.

EXAMPLE 19

Orange Sweet Potato Imitation Mayonnaise

Combine 47.6 g orange sweet potato flour, 6.5 g salt, and 113.25 g cold water until well blended. Add slowly to 340 g boiling water, stirring constantly. Continue stirring until mixture is completely gelatinized and thickened; cool to about 50 ° F.. Place mixture in conventional high speed blending device; add 200 g oil, (optional: 21.3 g lemon juice, vinegar, or ascorbic acid solution). Mix materials on highest speed until well blended, smooth, and uniform consistency. Mayonnaise will thicken as it cools.

EXAMPLE NUMBER 20

Orange Sweet Potato Milk

Combine 453 g water and 76.2 g orange sweet potato flour, mix thoroughly. Stirring constantly, heat until well gelatinized, thick, and well blended. Blend together an additional 453 g water, 76.2 g moderately fine to superfine orange sweet potato flour, and 37.5 g oil in any high speed blending device. Add in the cooked flour mixture. Blend 1–30 minutes at highest speeds, preferably 4 minutes. May be strained if flour not sufficiently fine.

EXAMPLE NUMBER 21

Orange Sweet Potato Milk Shake

Combine 76.2 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50 ° F. or lower, preferably 35 ° F.. In high speed blending device, combine gelatinized mixture, 12.5 g oil, 76.2 g orange sweet potato flour, and 226.5 g crushed ice. Blend well at speeds high enough to partially freeze mixture as ice particles become crushed and fine to form a thick slurry the consistency of a milk shake.

The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 152.4 g flour, 453 g water and 12.5 g oil (226.5 g water and all flour still cooked as described above) under conditions of freezing and then mixing to form a milk shake-like slurry without adding crushed ice. Similarly other methods of the art may be used to produce the frozen slurry.

EXAMPLE NUMBER 22

Orange Sweet Potato Ice Cream

The milk shake-like product described in example 21 may be used as a base for ice cream products. The above slurry is subjected to freezing at temperatures ranging from 32° F. to −30° F. or lower preferably −20–0° F. until product becomes frozen. The frozen mixture is then pulverized, placed in high speed blending equipment and blended at highest speeds until well mixed, smooth. and creamy. Freezing, pulverizing and mixing cycles may be repeated as desired. two such cycles are preferred. Additional embodiments described in Example 21 may also be used in this example.

EXAMPLE NUMBER 23

Orange Sweet Potato Pasta

Using conventional equipment for kneading thick dough, combine 453 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g orange sweet potato flour and 120 g water may be cooked to a thick paste and added to the above mixture.

In another alternative process, prior to extruding, the flour mixture described above which may or may not be simultaneously kneaded, may be maintained at temperatures above 50° C. for 2-30 minutes, preferably 2-5 minutes at 95° C. to gelatinize part of all of the dough.

When cooking, immerse noodles in boiling water for 2-10 minutes depending on width of noodles. Any other cooking techniques of the art may also be used. Noodles will change from off-white opaque to light brown as the starch granules gelatinize. Noodles may be used in any type pasta dish—soups, stews, pasta and sauce dishes, and the like.

EXAMPLE NUMBER 24

Orange Sweet Potato Crackers

In any suitable machine for mixing heavy doughs, combine 453 g orange sweet potato flour, 453 g water. 3.25 g salt. 75 g oil. and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like.

Alternatively, omit oil, or oil and salt, increasing water by 30 grams.

Alternatively, use binders, flours, sweeteners, extenders, flavorings, seasonings, fillers and other ingredients common to the art to produce a hyperallergenic cracker.

EXAMPLE 25

Orange Sweet Potato Pudding

Combine equal parts by volume of cooked, mashed orange sweet potato and water, using 1 liter of each. The method of cooking and pureeing may be by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are comminuted to a thick paste by any conventional means. Separately 152.4 g orange sweet potato flour is combined with 1 Kg water and heated to boiling point for 5 minutes to produce a thick gelatinized paste. The gelatinized paste is combined with the cooked tuber paste by any conventional mixing technique until well blended. The mixture is the consistency of pudding, and with the addition of no other ingredients has a pleasant, sweet taste. This is not to preclude the use of other ingredients commonly used as ingredients in pudding such as eggs, milk, conventional flours, oil, sweeteners, flavorants, spices, seasonings, of any kind in this invention.

Pudding can also be made by combining 453 g water and 76.2 g flour in suitable heating apparatus. As mixture reaches boiling stir constantly. When thoroughly gelatinized, very thick, put in high speed bleeding device and mix on high for 5 minutes. Add 25 g oil and mix again. Cool almost to freezing.

EXAMPLE 26

Orange Sweet Potato Flour

Thinly peel orange sweet potatoes under running water, also removing any spots, undesirable areas, then free of excess water, dip briefly in distilled water, again remove excess; do not soak. Shred to desired size, place on glass or metal trays; air dry at 145° F. for 8-12 hours, preferably 10. Comminute shreds with any desired technique that in addition to starch incorporates most of the fiber and other non-farinaceous material, 100% utilization is preferred, into the flour product that is at least a moderately fine flour.

EXAMPLE 27

Cooked Orange Sweet Potato Flour

The method of example 28 is used to produce a cooked flour product, with the added process of heating the orange sweet potato tuber with steam until gelatinized, and then proceeding with shredding and drying steps.

Other tubers of family Convolvulaceae such as white sweet potatoes and others can be used in the same proportions and in the same manner as previously described for orange sweet potatoes.

Having now fully described the invention, it will be apparent to one of ordinary skill in the art that many changes and modifications can be made thereto without departing from the spirit of the invention as set forth herein.

What is claimed as and so intended to be secured by Letters Patent is:

1. A flour of tubers of the family Convolvulaceae, wherein the flour consists essentially of the entire tuber, including substantially all of the flesh and fiber portions of said tuber, comminuted to a size so that substantially all of said comminuted tuber will pass through a screen of 0.015 inch opening, said flour having a moisture content of less than 20% by weight.

2. A non-grain edible flour possessing the ability to maintain a risen structure in the absence of grain flour, legume flour, or added fiber; said non-grain edible flour consisting essentially of the comminuted particles of tubers of family Convolvulaceae, including substantially all of the flesh and fiber of said tubers, comminuted to a size such that substantially all of said particles pass through a screen opening of 0.015 inch, wherein said flour has a moisture content of less than 20% by weight.

3. The flour of claim 2 wherein the flour is from sweet potatoes of the family Convolvulaceae.

4. The flour of claim 2 wherein the flour is from tubers at least more deeply colored than light-fleshed tubers of the family Convolvulaceae.

5. The flour of claim 2 wherein substantially all of the flour passes through a screen opening of 0.001 inch.

6. A milk substitute comprising water and the flour of claim 2 in amounts effective to produce said milk substitute.

7. An ice cream substitute formed by freezing the milk substitute of claim 6.

8. An imitation nut butter product comprising oil and the flour of claim 2 in amounts effective to produce said nut butter.

9. An infant formula comprising the flour of claim 2 in amounts effective to produce said infant formula.

10. A baked product comprising the flour of claim 2, water; and
leavening agent,
in amounts effective to produce said baked product.

11. An extruded product comprising water and the flour of claim 2 in amounts effective to produce said extruded product.

12. A colloidal product comprising the flour of claim 2;
an oil; and
water,
in amounts effective to produce said colloidal product.

13. A fried product comprising the flour of claim 2, an oil; and
water,
in amounts effective to produce said fried product.

14. A batter-type product comprising the flour of claim 2;
an oil; and
water,
in amounts effective to produce said batter-type product.

15. The flour of claim 2 wherein the flour is from tubers with light-colored flesh of the family Convolvulaceae.

* * * * *